United States Patent
Schaenzer (12)

(10) Patent No.: US 6,295,476 B1
(45) Date of Patent: Sep. 25, 2001

(54) MEDICAL LEAD CONDUCTOR FRACTURE VISUALIZATION METHOD AND APPARATUS

(75) Inventor: David G. Schaenzer, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/430,864

(22) Filed: Nov. 1, 1999

(51) Int. Cl.[7] ..................................................... A61N 1/05
(52) U.S. Cl. .......................................... 607/122; 600/374
(58) Field of Search .................................... 607/122, 123, 607/27, 28; 600/3, 377, 374

(56) References Cited

U.S. PATENT DOCUMENTS

| | | |
|---|---|---|
| 4,608,986 | 9/1986 | Beranek et al. . |
| 4,640,983 | 2/1987 | Comte . |
| 4,706,681 * | 11/1987 | Breyer et al. . |
| 4,964,414 | 10/1990 | Handa et al. . |
| 5,007,435 | 4/1991 | Doan et al. . |
| 5,059,166 | 10/1991 | Fischell et al. . |
| 5,199,939 | 4/1993 | Dake et al. . |
| 5,246,014 | 9/1993 | Williams et al. . |
| 5,322,499 | 6/1994 | Liprie . |
| 5,324,321 | 6/1994 | Pohndorf et al. . |
| 5,483,022 | 1/1996 | Mar . |
| 5,498,227 | 3/1996 | Mawad . |
| 5,545,203 | 8/1996 | Doan . |
| 5,584,873 | 12/1996 | Shoberg et al. . |
| 5,755,739 | 5/1998 | Sun et al. . |
| 5,760,341 | 6/1998 | Laske et al. . |
| 5,807,231 | 9/1998 | Liprie . |
| 5,824,077 | 10/1998 | Mayer . |
| 5,833,593 | 11/1998 | Liprie . |
| 5,855,546 | 1/1999 | Hastings et al. . |

* cited by examiner

Primary Examiner—Scott M. Getzow
(74) Attorney, Agent, or Firm—Beth L. McMahon (57) ABSTRACT

Methods for sensing or electrical stimulation of body organs or tissues are disclosed wherein a lead conductor wire or filament of a stranded lead conductor generates a radioactive emission when it is fractured sufficiently or is completely broken. The conductor wire or filament is formed of an inner core and an outer sheath surrounding the inner core, wherein the inner core is irradiated or is formed of a radioactive isotope in an alloy that provides an enhanced radiopaque aura when the sheath is fractured and the inner core is exposed. When the conductor wire or filament is intact, the radioactive inner core is fully encased within the outer sheath, and the outer sheath blocks or reduces radioactive emission along its length to a constant, relatively low level. In use, the emission is detected externally to the body, and the detection signifies that a fracture or break has occurred. Such leads preferably comprise cardiac leads for delivering electrical stimulation to the heart, e.g., pacing pulses and cardioversion/defibrillation shocks, and/or sensing the cardiac electrogram, having multiple lead conductors encased in a lead body subject to fracture under stress. The lead conductors can comprise mono-filar or multi-filar, parallel wound, coiled wires that arranged in a co-axial manner or in a side-by-side arrangement within the lead body. Or the straight or coiled lead conductors can be formed of a strand comprising a plurality of outer filaments wound helically about a central core filament or of a cable comprising a plurality of such peripheral strands wound helically about a central core strand. At least the outer filaments of a stranded conductor and peripheral strands of a conductor cable are formed with the radioactive core.

21 Claims, 4 Drawing Sheets

MEDICAL LEAD CONDUCTOR FRACTURE VISUALIZATION METHOD AND APPARATUS

FIELD OF THE INVENTION

The present invention relates to medical electrical leads for sensing or electrical stimulation of body organs or tissues and their method of fabrication and use, such leads having multiple electrical conductors encased in a lead body subject to fracture under stress, and particularly to implantable cardiac leads for delivering electrical stimulation to the heart, e.g., pacing pulses and cardioversion/defibrillation shocks, and/or sensing the cardiac electrogram or other physiologic data.

BACKGROUND OF THE INVENTION

Implantable medical electrical stimulation and/or sensing leads are well known in the fields of cardiac stimulation and monitoring, including cardiac pacing and cardioversion/defibrillation, and in other fields of electrical stimulation or monitoring of electrical signals or other physiologic parameters of the body. A pacemaker or cardioverter/defibrillator implantable pulse generator (IPG) or a cardiac monitor is typically coupled to the heart through one or more of such endocardial leads. The proximal end of such leads typically is formed with a connector, which connects to a terminal of the IPG or monitor. The lead body typically comprises one or more insulated, conductive wire surrounded by an insulating outer sleeve. Each conductive wire couples a proximal lead connector element with a distal stimulation and/or sensing electrode. An endocardial cardiac lead having a single stimulation and/or sensing electrode at the distal lead end and a single conductive wire is referred to as a unipolar lead. An endocardial cardiac lead having two or more stimulation and/or sensing electrodes at the distal lead end and two or more conductive wires is referred to as a bipolar lead or a multi-polar lead, respectively.

In order to implant an endocardial lead within a heart chamber, a transvenous approach is utilized wherein the lead is inserted into and passed through a pathway comprising the subclavian, jugular, or cephalic vein and through the superior vena cava into the right atrium or ventricle. It is necessary to accurately position the sense and/or stimulation electrode surface against the endocardium or within the myocardium at the desired site in order to achieve reliable sensing of the cardiac electrogram and/or to apply stimulation that effectively paces or cardioverts the heart chamber. The desired heart sites include the right atrium, typically the right atrial appendage, the right ventricle, typically the ventricular apex, and the coronary sinus and great vein descending therefrom.

The implantable cardiac lead conductor that has been typically employed in pacing leads or in early cardioversion/defibrillation leads is a single coiled wire or a multi-filar wire coil used alone in the unipolar lead configuration or used in a pair, co-axially arranged and insulated from one another, in a bipolar lead configuration. The coiled wires of such lead conductors may be formed of a single conductive metal or alloy material, e.g. MP35N alloy. Or the coiled wires have been formed of a composite conductive material, typically a silver core wire clad with MP35N alloy or surgical grade stainless steel or the like in a drawn brazed stranded (DBS) or drawn filled tube (DFT) fabrication process well known in the art, to provide increased conductivity while reducing the wire cross-section. An exemplary multi-filar wire coil as shown in commonly assigned U.S. Pat. No. 5,007,435, incorporated herein by reference.

Over the years many improvements have been made in lead bodies in the effort to include more than two lead conductors capable of carrying more current, and to make the lead body diameters smaller, more flexible, and more resistant to fracture. In the implantation of a cardiac device of the types listed above, and in the replacement of previously implanted cardiac leads, two or more transvenous cardiac leads are typically introduced through the venous system into the right chambers or coronary sinus of the heart. It has long been desired to minimize the diameter of the transvenous cardiac lead body to facilitate the introduction of several cardiac leads by the same transvenous approach. Moreover, a number of multi-polar, endocardial cardiac leads have been designed to accommodate more than two electrodes or to make electrical connection with other components, e.g., blood pressure sensors, temperature sensors, pH sensors, or the like, in the distal portion of the lead. In addition, endocardial cardioversion/defibrillation leads were developed for unipolar or bipolar pacing and sensing functions and for delivering cardioversion/defibrillation shocks to a heart chamber intended to be implanted in a heart chamber or a cardiac blood vessel, e.g., the coronary sinus.

The increased number of separate polarity and insulated coiled wire conductors is difficult to accommodate in the conventional coaxial coiled wire conductor winding arrangement having a desired, small, lead body outer diameter. One approach involved the use of separately insulated, coiled wire conductors that are parallel-wound with a common diameter and are separately coupled between a proximal connector element and to a distal electrode or terminal.

It has also been proposed to diminish the lead body diameter further by eliminating the lumen for receiving the stiffening stylet and by replacing the large diameter coiled wire conductors with highly conductive stranded filament wires or cables formed of a plurality of such wires. In bipolar or multi-polar leads, each such wire or cable extends through a separate lumen extending in parallel within a lead body sheath that maintains electrical isolation between them. Examples of such lead body insulating sheaths formed to enclose a plurality of straight, typically stranded, wire lead conductors, miniaturized coiled wire conductors or combinations of such straight and coiled wire conductors are disclosed in U.S. Pat. Nos. 4,608,986, 5,324,321, 5,545,203, and 5,584,873, all incorporated herein by reference. These patents and U.S. Pat. Nos. 4,640,983, 4,964,414, 5,246,014, 5,483,022, and 5,760,341, all incorporated herein by reference, present a number of alternative designs of such stranded filament wires or cables. As shown therein, the stranded filaments are formed of highly conductive alloys and used in small diameter lead bodies in either a straight configuration or a in coiled configuration. When straight conductors are employed, it is necessary to resort to use of an introducer rather than the stylet to pass the lead through the vessel paths identified above and to position and fix the distal electrode of the lead at the desired site in the heart chamber. In the coiled configuration, a plurality of stranded filament conductors are wound into a like plurality of intertwined, parallel wound, coils that are electrically connected together in a redundant manner as disclosed in the above-incorporated '983 and '022 patents.

In these patents, complex cables are formed of a number of filaments of single alloy material or of filaments formed with an inner core of one material e.g., silver or stainless steel, and an outer sheath of another material, e.g., MP35N, using the DBS or DFT extrusion techniques. The current carrying capacity of cardioversion/defibrillation lead conductors formed in these ways is maximized for the cross-section dimensions of the filaments and cables.

These efforts to minimize lead body diameter, maximize lead body flexibility, the number of separate conductors encased in the lead body, the current carrying capacity of each such conductor have to be balanced by retaining adequate resistance to fracture. The transvenous pathway can include a number of twists and turns, and the lead body can be forced against bony structures of the body that apply stress to It, causing the lead body to be crushed and/or causing the lead conductor to break. Moreover, the heart beats approximately 100,000 times per day or over 30 million times a year, and each beat stresses at least the distal portion of the lead body located within a heart chamber or cardiac vessel. Over the years of implantation, the lead conductors and insulation are subjected to such cumulative mechanical stresses that can result in degradation of the insulation or fractures of the lead conductors with untoward effects on device performance and patient well being.

For, example, the percutaneous subclavian, venipuncture approach is commonly employed in the implantation of endocardial pacing leads or cardioversion/defibrillation leads, and it involves passing the lead body through the costoclavicular region where it can be crushed as described in U.S. Pat. No. 5,545,203, incorporated herein by reference. Efforts have been undertaken to improve the crush resistance of lead bodies that encase a plurality of straight or coiled lead conductors as described in the '203 patent or in commonly assigned U.S. Pat. No. 5,584,873, incorporated herein by reference.

However, despite these improvements, not all causes of lead fracture can be overcome by lead body design, and lead conductor fractures still occur from time to time. Fractures that occur in multi-filar or stranded filament lead conductor wires or cables, typically commence with less than all of the filaments. Lead conductivity may decrease as a result, and the reduced conductivity affects sensing and current stimulation efficacy. Moreover, the broken wire or filament ends may make intermittent contact, resulting in erratic conductivity changes.

The resulting system performance deteriorates, but the drop in performance may go unnoticed for a time until a complete break occurs. When system performance deterioration becomes symptomatic, it is often difficult to determine that it is due to a lead conductor fracture. The lead conductor wires or filaments or a cable are so small that it is typically not possible to visualize the break under fluoroscopy, although complete separations of the broken ends of a lead conductor have been observed in this manner. But, such complete separations usually follow earlier conductor fractures, and it is much preferable to be able to diagnose a lead conductor fracture at the earlier stages and to replace the lead before the patient is endangered.

SUMMARY OF THE INVENTION

The present invention addresses these problems by providing a lead conductor wire or filament of a stranded lead conductor that generates a radioactive emission when it is fractured sufficiently to expose its core or is completely broken and detecting the emission to thereby determine that such a fracture or break has occurred.

The present invention employs a conductor wire or filament having an inner core and an outer sheath surrounding the inner core, wherein the inner core is irradiated or is formed of a radioactive alloy that provides an fluoroscopically visible aura when the sheath is fractured and the inner core is exposed and/or emits radiation detectable external to the patient. When the conductor wire or filament is intact, the radioactive inner core is fully encased within the outer sheath, and the outer sheath blocks or reduces radioactive emission along its length to a constant, relatively low level.

The radioactive materials are preferably X-ray and/or beta emitters having relatively long half lives that allow the radioactive emission to be seen or detected over a period of years of implantation in the typical patient. However, the level of emissions that are released when the outer sheath is fractured or completely severed is no more than the levels that are typically employed in therapeutic implants of radioactive wires.

The present invention is preferably implemented into coiled wire lead conductors formed of mono-filar or multi-filar, parallel wound coiled wires that arranged in a co-axial manner or in a side-by-side arrangement within the lead body. Or the present invention can be implemented in straight or coiled lead conductors each formed of a strand comprising a plurality of outer filaments wound helically about a central core filament or each comprising a cable formed of a plurality of such peripheral strands wound helically about a central core strand. At least the outer filaments of a stranded conductor and peripheral strands of a conductor cable are formed with the radioactive core.

In use, the fracture or complete breakage of such a lead conductor wire or filament can be readily detected. If even a minute fracture occurring along only one side of the outer sheath of the wire or filament occurs, it will allow radiation to escape through the fracture. X-ray emissions are detectable as a bright spot in a fluoroscopic image or X-ray image of the lead body. Beta emissions may be detected external to the body using a dosimeter, Geiger counter, or the like. In this way, minute fractures can be detected even before the lead conductor is fully severed.

This summary of the invention and the advantages and features thereof have been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate like or identical structures throughout the several views, and wherein.

DETAILED DESCRIPTION OF THE PREFERRED EMBODIMENTS OF THE INVENTION

The present invention finds particular utility in the fabrication and implantation of cardiac leads, e.g., atrial and/or ventricular pacing leads and/or cardioversion/defibrillation leads having elongated lead bodies and lead conductors that are subject to fracture. Preferred embodiments of such lead conductor fabrications and implantations of such endocardial cardiac leads that are implanted transvenously will be described in detail. But, it is to be understood that the present invention is not limited to the same. The present invention can be implemented in the fabrication and use of other epicardial cardiac leads that are implanted subcutaneously and in electrical leads intended to be disposed within the patient's body, including nerve, brain, organ, and muscle stimulation leads.

Figure 1:
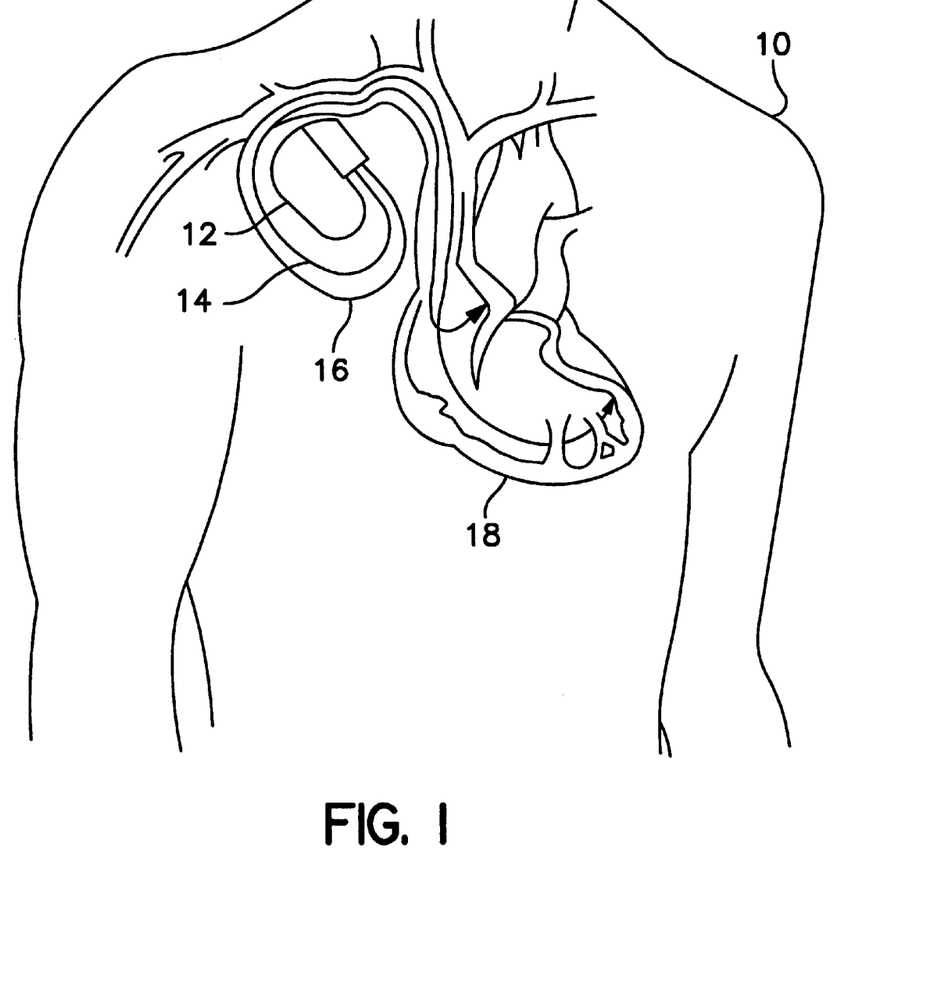
FIG. 1 is a schematic illustration of a typical implantation of an IPG and endocardial lead system in which the lead conductor construction and method of fracture detection of present invention is implemented.

FIG. 1 depicts a typical arrangement of a pacing or implantable cardioverter/defibrillator (ICD) system implanted in a patient 10, the system comprising a subcutaneously disposed implantable pulse generator (IPG) 12 and one or more endocardial atrial lead 14 and ventricular lead 16. The IPG 12 is implanted in a subcutaneous location in the upper chest as shown in FIG. 1 or in the abdomen, and the proximal ends of the endocardial leads 14 and 16 are coupled with it. The distal end of atrial lead 14 bearing one or more atrial pace/sense electrode is shown disposed generally in the atrial region of the patient's heart 18. The distal end of ventricular lead 16 bearing one or more pace/sense electrode is disposed generally in the ventricular region of heart 18. The distal end of lead 14 can also be disposed in the coronary sinus and even extend into a branching vein of the coronary sinus to dispose one or more distal pace/sense electrode in relation to the atrium or the ventricle to function as an atrial or ventricular pace/sense lead in a manner well known in the art. Alternatively, one or more of the leads 14 and 16 can disposed epicardially about the heart 18. Moreover, one or more of the endocardial leads 14 and 16 can include a cardioversion/defibrillation electrode disposed at any of the above described locations.

Figure 2:
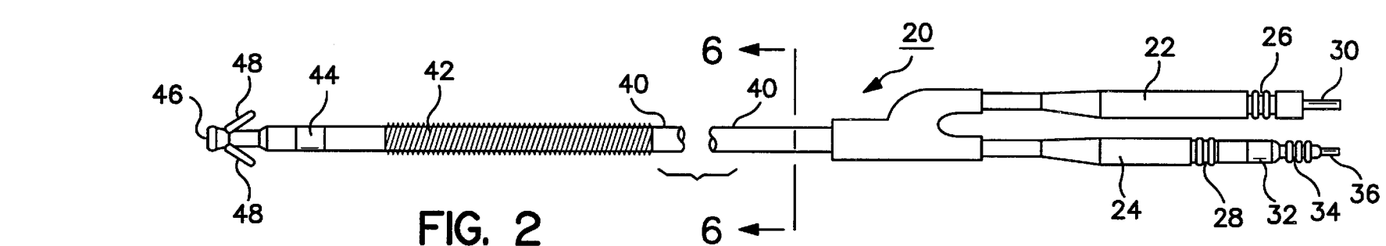
FIG. 2 is a plan view of a typical endocardial pacing and cardioversion/defibrillation lead that incorporates the lead conductors of the present invention.

An exemplary cardioversion/defibrillation lead 20 in which the present invention may be advantageously implemented and that can be used in the locations of endocardial leads 14 and 16 is depicted in FIG. 2. Lead 20 is provided with an elongated insulating lead body 40, preferably fabricated of a bio-compatible elastomer, e.g., silicone rubber, polyurethane, etc., and enclosing three lead conductors. Although not visible in FIG. 2, it should be noted that the elongated conductors passing through lead body 40 may be any of the various known available conductors for use in conjunction with implantable electrical leads, including mono-filar or multi-filar coiled wire conductors, stranded wires formed of filaments, and the like as further described below with reference to FIGS. 6 and 7.

An elongated cardioversion/defibrillation electrode 42, a pace/sense ring electrode 44, and a pace/sense tip electrode 46 are supported along a distal segment of the lead body 40 and are each coupled to a lead conductor located within the lead body 40. Electrodes 42, 44 and 46 may correspond to any conventionally available pace/sense and cardioversion/defibrillation electrodes. When the lead 20 is intended for implantation in the right ventricular chamber, a fixation mechanism, e.g. the depicted soft, pliant tines 48 are provided to be lodged within right ventricular trabeculae to maintain electrode 46 in contact with the endocardium of the right ventricle. Alternatively, an active fixation mechanism, e.g., a retractable and rotatable helix, can be substituted for the tines 48, and the distal tip electrode can be fixed in the right atrial or ventricular heart chamber. The distal electrodes of the lead 40 can also be advanced into a cardiac vessel, e.g., the coronary sinus, if no fixation mechanism is provided.

A connector assembly is formed at the proximal end of the lead body 40 for making electrical and mechanical connection with the IPG 12 of FIG. 1 in a manner well known in the art. The connector assembly comprises a molded lead bifurcation, which splits off two of the conductors within lead body 40 coupled to the distal pace/sense electrodes 44 and 46 to a bipolar, in-line connector assembly 24, which generally corresponds to the IS1 connector standard for pacing leads. Connector assembly 24 is provided with a first set of sealing rings 28, a connector ring 32, a second set of sealing rings 34, and connector pin 36. Connector pin 36 is coupled to the lead conductor that extends through the lead body 40 to the distal tip electrode 46. The connector ring 32 is coupled to the lead conductor that extends through the lead body 40 to pace/sense ring electrode 44. The lead conductor coupled to cardioversion/defibrillation electrode 42 extends to connector assembly 22, which comprises a set of sealing rings, 26 and a connector pin 36. The illustrated connector assemblies 22 and 24 are conventional elements and may correspond to any of the numerous known electrical connector assemblies provided on implantable medical leads.

In the specific context of the lead 20 illustrated in FIG. 2, the lead conductor coupling connector pin 32 to distal electrode 16 preferably takes the form of a multi-filar, wire coil to allow passage of a stylet through a lumen of the wire coil. The lead conductors coupling ring electrode 14 to connector ring 32 and coupling the cardioversion/defibrillation electrode 12 to connector pin 30 preferably take the same form or the form of stranded cables formed of wire filaments. The present invention is believed workable in the context of any of the numerous conductors known for use in implantable electrical leads, in any combination with one another.

In accordance with the present invention, at least one conductor wire or filament of a strand or cable within the lead body 40 is formed of an inner core surrounded by an outer sheath, and the inner core is irradiated or is formed of a radioactive alloy that provides an fluoroscopically visible aura or releases radiation otherwise detectable outside the patient's body when the sheath is fractured and the inner core is exposed. When the conductor wire or filament is intact, the radioactive inner core is fully encased within the outer sheath. The intact outer sheath blocks or allows extremely low intensity radioactive emissions at a constant intensity along the length of the lead conductor. However, even a minute fracture occurring along only one side of the outer sheath will allow higher intensity radioactive emissions to escape through the fracture.

Figure 3:
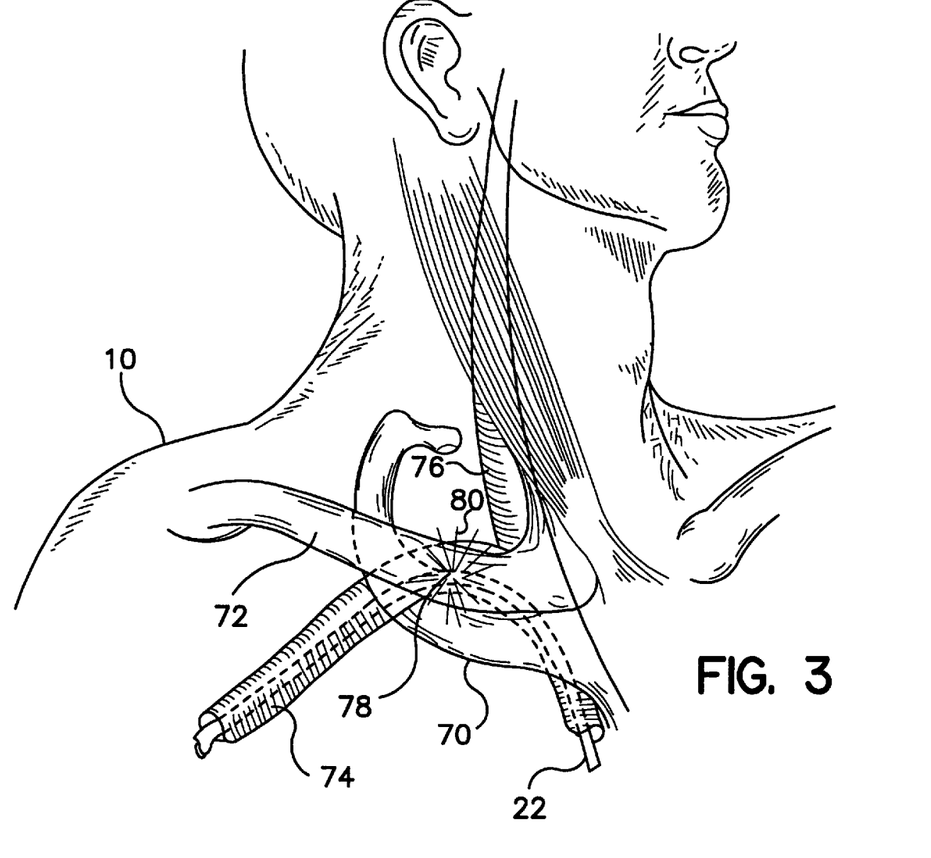
FIG. 3 is a schematic illustration of the emission of radiation at a fracture of a lead conductor of the exemplary lead of FIG. 2 that can be observed under fluoroscopy or in an X-ray image or otherwise.

FIG. 3 illustrates the transvenous subclavian route of a portion of an endocardial lead body 40 of the type illustrated in FIGS. 1 and 2 and the emission of a minute quantity of X-ray and/or optionally other types of radiation from the radioactive core exposed through a fracture of the outer sheath or due to a complete breakage of a conductor wire or filament of the lead body 40. The lead body 40 is extended through subclavian vein 74, which passes between the first rib 70 and the right clavicle 72 before joining the internal jugular vein 76. Frequently the subclavian vein 74 and the space between the first rib 70 and the right clavicle 72 must accommodate two or more lead bodies as shown in FIG. 1. As noted in the above-incorporated '203 patent, crushing pressures can sometimes be exerted against the lead body 20 by patient body movements that bring the first rib 70 and the right clavicle 72 closer together than at the time of implantation.

In accordance with the method of use and lead body construction of the present invention, the lead conductors normally do not emit appreciable radiation into the patient's body 10 while they are not damaged. But even a minute fracture 78 of the lead conductor causes the radioactive emission 80 into the adjacent tissues. The emission 80 is readily detected as a bright spot in a fluoroscopic image or X-ray image of the lead conductors within lead body 20. In this way, minute fractures 78 can be detected even before the lead conductor is fully severed.

Figure 4:
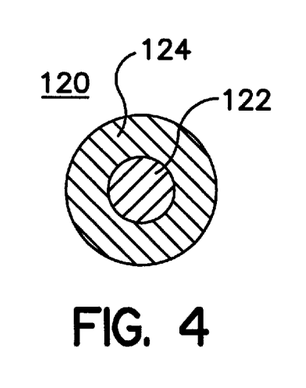
FIG. 4 is a cross-section view of an intact lead conductor wire or filament formed in accordance with the present invention.
Figure 5:
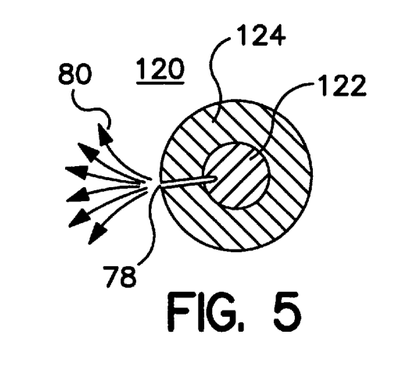
FIG. 5 is a cross-section view of a fractured lead conductor wire or filament formed in accordance with the present invention, wherein radiation is emitted through the fracture.

FIG. 4 depicts one such lead conductor wire or filament 120 comprising a radioactive inner core 122 surrounded by an outer sheath 124. A minute constant background emission of radiation may occur through the outer sheath 124 while it is not breached. FIG. 5 depicts the lead conductor wire or filament 120 of FIG. 4 with a minute crack 78 formed in the outer sheath 124 exposing the radioactive inner core 122 and allowing the radioactive emission 80 to occur.

The radioactive materials are preferably X-ray and/or beta emitters having half lives of at least one year, preferably of two years or more, that allow the radiation emission 80 to be seen or detected over a period of years of implantation in the typical patient, preferably having a half life of at least two years. X-ray emitters may include iron 55, which isotope may be employed as part of the alloy from which the corel 122 is fabricated. For example, iron 55 may be employed in a stainless steel alloy otherwise conforming to alloys employed in implantable lead conductors, such as MP35N alloy. Beta emitters might include cobalt 60, which may similarly be incorporated into a stainless steel type alloy core. Curium 244 might be substituted cobalt 60 or Iron 55. The outer sheath 124 may be fabricated of alloys of the type typically employed in implantable conductors, such as MP35N alloy or Elgiloy, but should be free of radioactive isotopes.

The level of emissions that are released when the outer sheath 124 is fractured or completely should be no more than the levels that are typically employed in therapeutic implants of temporary radioactive wires and permanent radioactive implants, e.g., stents formed of radioactive wires. The fabrication and therapeutic implantation of such wires and implants made therefrom are widely published, as exemplified by U.S. Pat. Nos. 5,059,166, 5,176,617, 5,199,939, 5,322,499, 5,498,227, and 5,824,077, all incorporated herein by reference in their entireties. The '165 patent in particular discloses forming radioactive wires by coating the implant wire with a radioactive alloy or forming the wires of an inner core wire formed of radioactive material and an outer sheath that provides desirable strength and spring characteristics. The above-incorporated '077 patent describes a number of materials and fabrication techniques, including use of DFT fabrication techniques to form a radioactive inner core surrounded by a non-radioactive outer sheath.

The lead body 20 of the lead of FIG. 1 can be constructed in a wide variety of ways well known in the art of implantable leads. At a minimum, a single lead wire 120 of the type depicted in FIG. 4 can be employed to couple each distal electrode 42, 44, 46 with its respective proximal connector elements 30, 32 and 36, respectively. However, it is preferred that each conductor be formed of a multi-filar conductor wire formed of a plurality of filars or filaments to provide electrical redundancy and to increase flexibility and suppleness of the resulting lead body 40.

Figure 6:
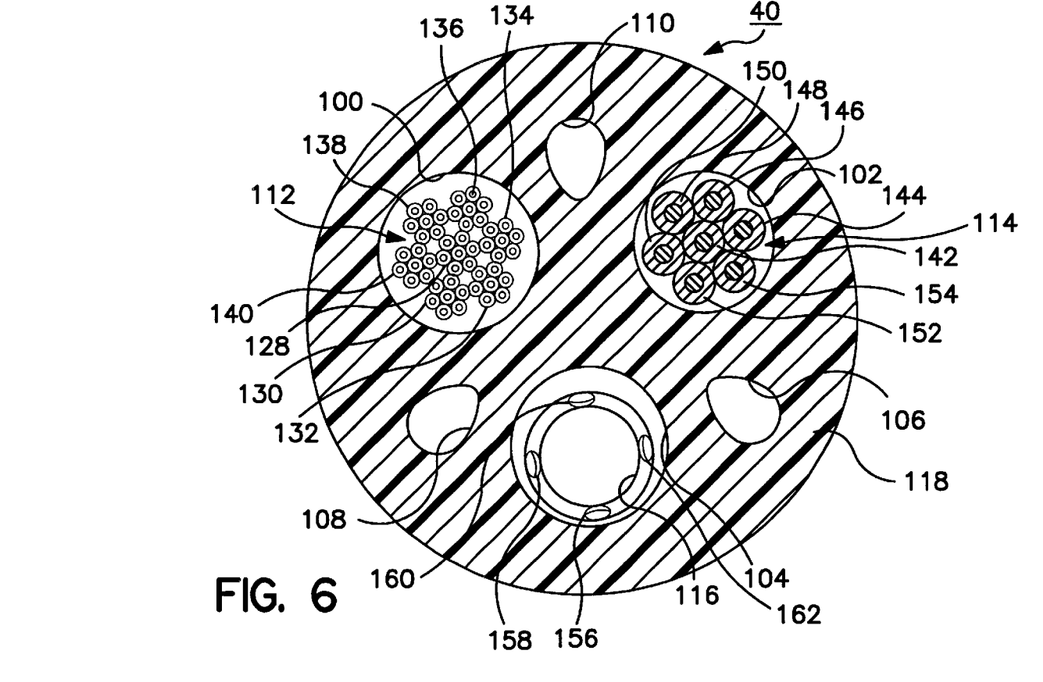
FIG. 6 is a cross-section view taken along lines 6—6 of FIG. 2 illustrating one form of lead body enclosing various types of straight and coiled lead conductors formed of lead conductor wires or filaments of the invention illustrated in FIG. 4.

FIG. 6 illustrates a cross-section through lead body 40 illustrating forms that the three lead conductors can optionally take. The lead body 40 is formed in the manner disclosed in the above-incorporated '873 patent of a single extruded tube 118 of a bio-compatible, electrically insulating elastomer, e.g., polyurethane, and lead conductors 112, 114 and 116. The tube 118 is extruded with three spaced apart conductor lumens 100, 102 and 104 containing the respective lead conductors 112, 114 and 116 and with three compression lumens 106,108 and 110 between the conductor lumens 100, 102 and 104 that function in the manner disclosed in the above-incorporated '873 patent. The compression lumens 106, 108, 110 have utility in absorbing stresses placed on the lead body but need not be present in the practice of the present invention.

All of the lead conductors 112, 114 and 116 illustrated in the cross-section view of FIG. 6 are formed in an electrically redundant manner of a plurality of wire coiled wires or stranded wire filaments that are coated on their exterior surfaces with PTFE to facilitate inserting the lead conductors through the lead conductor lumens. At least one filament of each strand of lead conductors 112 and 114 or wire of each coiled wire of lead conductor 116 is formed of the radioactive inner core 122 surrounded by the outer sheath 124 of wire or filament 120 depicted in FIG. 4. However, it is preferred that a plurality or all of the coiled wires of lead conductor 116 and the stranded wire filaments of lead conductors 112 and 114 are formed of the radioactive inner core 120 surrounded by the outer sheath 122.

Two different versions of straight lead conductors 112 and 114 are depicted in the lead lumens 100 and 102, respectively, of FIG. 6. Each of the straight conductors 112 and 114 may take the form of a bundled, stranded filament conductors disclosed in the above-incorporated '986 and '321 patents or the '829 application, for example. The invention may also be practiced using any of the numerous other stranded filament conductors known to the art. The stranded filament conductors of the present invention can also be wound into a plurality of intertwined, parallel wound, coils that are electrically connected together as described above with respect to the above-incorporated '983 and '022 patents, for example.

The lead conductor 114 is formed of a straight, inner core filament 142 surrounded by six outer filaments 144, 146, 148, 150, 152 and 154 helically wound into a single 1×7 wire strand or cable. The six outer filaments 144, 146, 148, 150, 152 and 154 are more likely to break or fracture earlier under bending stress than the inner core filament 142, and therefore the inner core filament 142 could be fabricated without the radioactive core 122 of FIG. 4.

The lead conductor 112 is formed in the manner described in the above-incorporated '414 patent of seven strands, and each strand is formed of seven filaments of smaller gauge than those forming lead conductor 114, resulting in a "7×7" wire cable of 49 total filaments. The straight, centrally disposed, core wire strand 128 is formed of six outer filaments helically wound around a straight inner core filament. The six outer or perimeter wire strands 130, 132, 134, 136, 138, and 140 are formed in the same manner as the core wire strand 128, that is, by an inner core filament surrounded by six outer filaments that are helically wound about it. The six outer or perimeter wire strands 130,132, 134,136,138, and 140 are themselves wound helically around the straight core wire strand 128. The six perimeter wire strands 130, 132, 134, 136, 138, and 140 of the 7×7 cable are more likely to break or fracture under bending stress earlier than the inner strand 128, and so the filaments of the inner strand 128 could be formed without the radioactive inner core 122 of FIG. 4.

Lead conductor 116 is formed in a parallel wound, multi-filar, coiled wire of the type disclosed in the above-incorporated '435 and '044 patents. Each of the four parallel wound wires 156, 158, 160 and 162 are formed with the radioactive core 122 surrounded and enclosed within the outer sheath 124 of FIG. 4.

Figure 7:
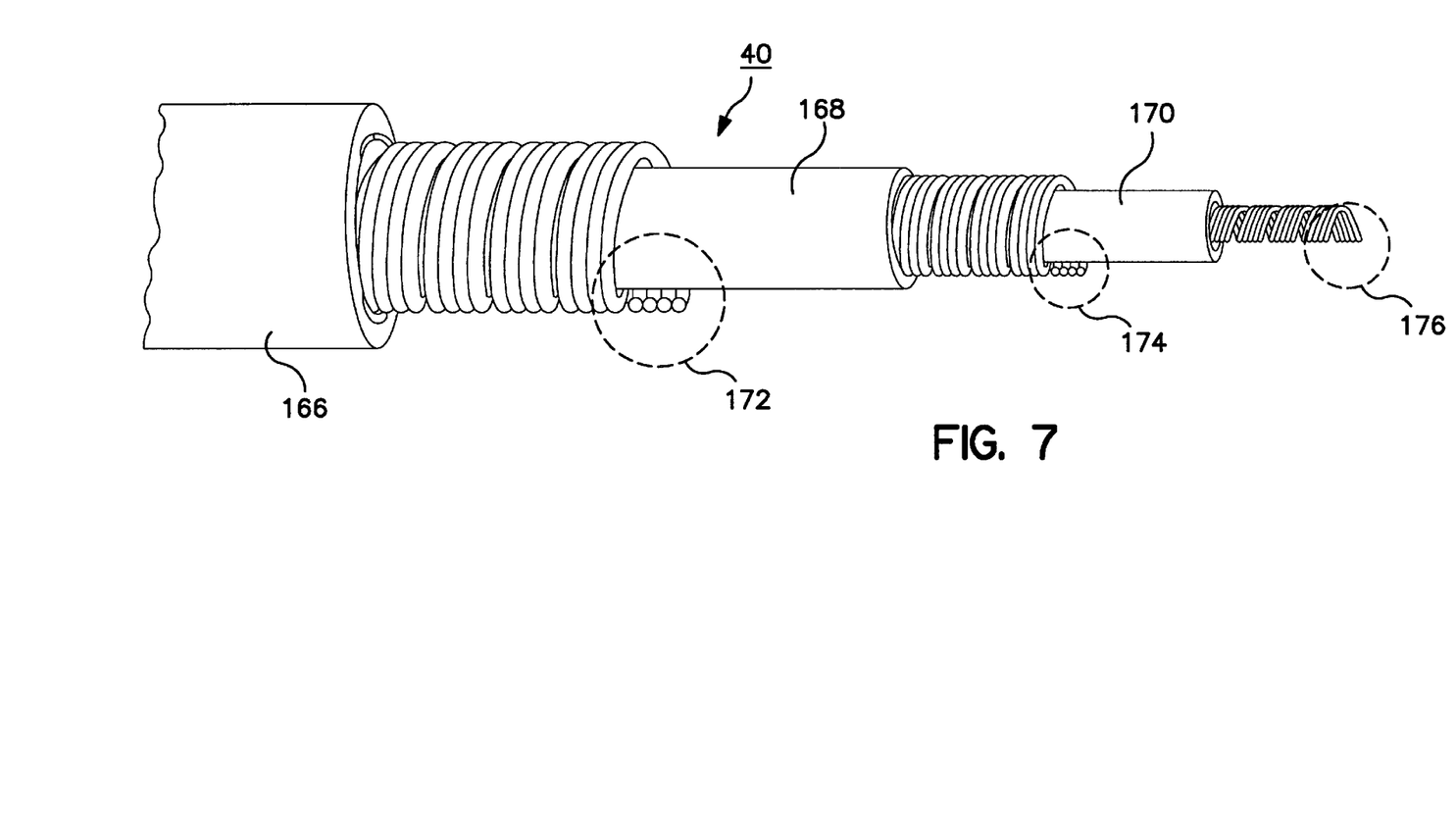
FIG. 7 is a partial sectional view taken along lines 7—7 of FIG. 2 illustrating a further form of lead body enclosing coiled lead conductors formed of lead conductor wires or filaments of the invention illustrated in FIG. 4.

FIG. 7 depicts a further variation of the construction of the lead body 40 wherein it is formed in a co-axial manner of three coiled wire conductors 172, 174 and 176 enclosed within outer insulating sheath 166 and separated by intermediate insulating sheath 168 and innermost tubular sheath 170. Each conductor 172, 174, 176 is formed of one or more, e.g., four, parallel wound wires like the parallel wound wires 156, 158, 160 and 162 of lead conductor 116. Each wire of each or certain ones of the coiled wire conductors 172, 174, and 176 can be formed as a single wire having the radioactive core 122 surrounded and enclosed within the outer sheath 124 as shown in FIG. 4. Alternatively, each wire of each or certain ones of the coiled wire conductors 172, 174, and 176 can be formed as a 1×7 filament strand in the manner described above with respect to conductor 114 or as a 7×7 strand cable in the manner described above with respect to conductor 112. Each wire or strand or cable of the coiled wire conductors 172, 174 and 176 can also be coated with an insulating material, e.g., PTFE.

A wide variety of lead body constructions having one or more lead conductor coupled between one or more distal electrode and proximal connector element in which the present invention can be implemented are known in the prior art.

In use, the lead 20 is implanted in the body 10 extending between the patient's heart 18 and the IPG 12 in the manner depicted in FIGS. 1 and optionally as depicted in FIG. 2. Periodically, the patient is examined by the physician who conducts sensing and pacing and/or cardioversion/defibrillation tests of the pacing and/or cardioversion/defibrillation functions. If an irregularity is noted in testing the efficacy of these therapies and/or sensing of the heart signals, the physician can observe the image of the implanted leads under fluoroscopy. Or an X-ray or fluoroscopic image of the implanted leads can be taken periodically even if there are no symptoms of lead fracture. A fracture that may or may not cause symptoms or the complete breakage of a lead conductor wire or strand or filament can be observed by the bright appearing fluoroscopic aura of the emission.

Although a number of lead conductor types are illustrated in the figures and described above, it will be understood that the present invention may be incorporated into the fabrication and use of any lead conductors of any type not explicitly described or depicted.

While particular embodiments of the invention have been disclosed herein in detail, this has been done for the purposes of illustration only, and is not intended to limit the scope of the invention as defined in the claims that follow. It is to be understood that various substitutions, alterations, or modifications can be made to the disclosed embodiment without departing from the spirit and scope of the claims. The above described implementations are simply those presently preferred or contemplated by the inventors, and are not to be taken as limiting the present invention to the disclosed embodiments. It is therefore to be understood, that within the scope of the appended claims, the invention may be practiced otherwise than as specifically described without actually departing from the spirit and scope of the present invention.

What is claimed is:

1. In a medical electrical lead for implantation within the body of the type comprising an elongated lead body enclosing at least one lead conductor extending in a lead body lumen between an electrode and a connector element, wherein the lead body and enclosed lead conductor are subject to stress that may cause the lead conductor to be fractured or broken, the improvement in the lead conductor comprising:

a source of radiation incorporated within the lead conductor that emits radiation from a fracture of break in the lead conductor.

2. The medical electrical lead of claim 1, wherein:

the lead conductor further comprises a conductor wire or filament formed of elongated inner core and an outer sheath surrounding the inner core; and the source of radiation comprises a radioactive isotope forming part of the inner core.

3. The medical electrical lead of claim 2, wherein the elongated inner core is fully encased within the outer sheath, and the outer sheath blocks or reduces radioactive emission along its length to a constant, relatively low level while the conductor wire or filament is intact.

4. The medical electrical lead of claim 3, wherein the lead conductor comprises a mono-filar coiled wire.

5. The medical electrical lead of claim 3, wherein the lead conductor comprises a multi-filar, parallel wound, coiled wire.

6. The medical electrical lead of claim 1, wherein:

the lead conductor comprises a strand comprising a plurality of outer filaments wound helically about a central core filament, at least one of the filaments is formed of an elongated inner core and an outer sheath surrounding the inner core; and the source of radiation further comprises a radioactive isotope forming part of the inner core.

7. The medical electrical lead of claim 6, wherein the lead conductor comprises a cable formed of a plurality of said strands arranged such that a central core strand is surrounded by a plurality of peripheral strands wound helically about said central core filament.

8. The medical electrical lead of claim 1, wherein:

the lead conductor comprises a strand comprising a plurality of outer filaments wound helically about a central core filament, the outer filaments are each formed of an elongated inner core and an outer sheath surrounding the inner core; and the source of radiation further comprises a radioactive isotope forming part of the inner core of at least one of the filaments.

9. The medical electrical lead of claim 1, wherein:

the lead conductor comprises a strand comprising a plurality of outer filaments wound helically about a central core filament, each of the filaments is formed of an elongated inner core and an outer sheath surrounding the inner core; and the source of radiation comprises a radioactive isotope forming part of each of the inner cores.

10. The medical electrical lead of claim 1, wherein:

the lead conductor comprises a cable formed of a plurality of strands of filaments, each strand comprising a plurality of outer filaments wound helically about a central core filament;

each of the plurality of strands comprises a central core strand and a plurality of peripheral strands wound helically about said central core filament;

at least one of the filaments is formed of elongated inner core and an outer sheath surrounding the inner core; and the source of radiation further comprises a radioactive alloy forming part of the inner core.

11. The medical electrical lead of claim 1, wherein:

the lead conductor comprises a cable formed of a plurality of strands of filaments, each strand comprising a plurality of outer filaments wound helically about a central core filament;

each of the plurality of strands comprises a central core strand and a plurality of peripheral strands wound helically about said central core strand;

each of the filaments forming the plurality of peripheral strands is formed of an elongated inner core and an outer sheath surrounding the inner core; and the source of radiation further comprises a radioactive alloy forming part of at least one of the inner cores.

12. The medical electrical lead of claim 1, wherein:

the lead conductor comprises a cable formed of a plurality of strands of filaments, each strand comprising a plurality of outer filaments wound helically about a central core filament;

each of the plurality of strands comprises a central core strand and a plurality of peripheral strands wound helically about said central core strand;

each of the filaments forming the plurality of strands is formed of an elongated inner core and an outer sheath surrounding the inner core; and the source of radiation further comprises a radioactive alloy forming part of each of the inner cores.

13. A method of determining when a lead conductor of a medical electrical lead, of the type comprising an elongated lead body enclosing at least one lead conductor extending in a lead body lumen between an electrode and a connector element that is implanted within the body, is fractured, the method comprising the steps of:

incorporating a source of radiation within the lead conductor that emits radiation from a fracture of break in the lead conductor;

implanting the lead in the body; and detecting any such emission of radiation from outside the body.

14. The method of claim 13, wherein the incorporating step further comprises the steps of:

forming the lead conductor of a conductor wire or filament with an elongated inner core and an outer sheath surrounding the inner core; and incorporating said source of radiation within the inner core.

15. The method of claim 13, wherein the lead conductor forming step further comprises the step of fully encasing the elongated inner core within the outer sheath.

16. The method of claim 13, wherein the incorporating step further comprises the steps of:

forming the lead conductor of a single conductor wire with an elongated inner core surrounded by an outer sheath;

incorporating said source of radiation within the inner core; and winding the lead conductor into a coil.

17. The method of claim 13, wherein the incorporating step further comprises the steps of:

forming the lead conductor of a plurality of conductor wires with each conductor wire having an elongated inner core surrounded by an outer sheath;

incorporating said source of radiation within the inner cores; and parallel winding the plurality of lead conductors into a multi-filar, parallel wound, coiled wire.

18. The method of claim 13, wherein the incorporating step further comprises the steps of:

forming at least one filament of an elongated inner core and an outer sheath surrounding the inner core;

incorporating said source of radiation within the inner; and winding a plurality of outer filaments helically about a central core filament the filament to form a strand of filaments.

19. The method of claim 18, wherein the incorporating step further comprises the step of winding a plurality of peripheral strands helically about a central core strand to form a cable of strands.

20. The method of claim 13, wherein the incorporating step further comprises the steps of:

forming a plurality of filaments each having an elongated inner core and an outer sheath surrounding the inner core;

incorporating said source of radiation within the inner; and winding a plurality of outer filaments helically about a central core filament the filament to form a strand of filaments.

21. The method of claim 20, wherein the incorporating step further comprises the step of winding a plurality of peripheral strands helically about a central core strand to form a cable of strands.

* * * * *

UNITED STATES PATENT AND TRADEMARK OFFICE
CERTIFICATE OF CORRECTION

PATENT NO. : 6,295,476 B1  
DATED : September 25, 2001  
INVENTOR(S) : David G. Schaenzer Page 1 of 1

It is certified that error appears in the above-identified patent and that said Letters Patent is hereby corrected as shown below:

Column 10,
Line 28, delete "of" and replace with -- or --.

Signed and Sealed this

Twenty-eighth Day of January, 2003

JAMES E. ROGAN
*Director of the United States Patent and Trademark Office*